United States Patent [19]

Takenaka et al.

[11] Patent Number: 5,141,935
[45] Date of Patent: Aug. 25, 1992

[54] DIHYDROBENZ THIAZINE DERIVATIVE AND MICROORGANISM CONTROL AGENT

[75] Inventors: Mitsuaki Takenaka; Masanori Watanabe, both of Ube, Japan

[73] Assignee: Ube Industries, Ltd., Ube, Japan

[21] Appl. No.: 411,847

[22] Filed: Sep. 25, 1989

[30] Foreign Application Priority Data

Oct. 7, 1988 [JP] Japan .............................. 63-252089

[51] Int. Cl.⁵ .................... C07D 279/16; A61K 31/54
[52] U.S. Cl. .................................. 514/224.2; 544/52
[58] Field of Search ........................ 544/52; 514/224.2

[56] References Cited

PUBLICATIONS

Prasad, Chemical Abstracts, vol. 70, entry 106447m (1969).
Prasad, J. Med. Chem., (1969), 12(2), 290–294.
Chemical Abstracts, 89: 215324g (1978).
Hori et al, Heterocycles, 9 (1978), 1413–1417.

Primary Examiner—John M. Ford
Attorney, Agent, or Firm—Frishauf, Holtz, Goodman & Woodward

[57] ABSTRACT

A compound represented by the formula:

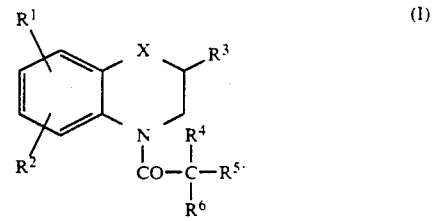

wherein
$R^1$ and $R^2$ each represent a hydrogen atom, a halogen atom, a nitro group, a lower alkyl group or a trifluoromethyl group; $R^3$ represents a hydrogen atom, a lower alkyl group, a phenyl group or a lower alkoxy-carbonyl group; $R^4$ and $R^5$ each represent a hydrogen atom or a lower alkyl group; $R^6$ represents a halogen atom; and X represents an oxygen atom or a sulfur atom, and a microorganism control agent, comprising the above compound as an active ingredient.

23 Claims, No Drawings

DIHYDROBENZ THIAZINE DERIVATIVE AND MICROORGANISM CONTROL AGENT

BACKGROUND OF THE INVENTION

1. Field of the Invention

This invention relates to a novel dihydrobenzothiazine or dihydrobenzoxazine derivative and a microorganism control agent containing the same.

2. Background Information

In the past, in circulation cooling water systems of factories, buildings, etc. and water systems of paper pulp making systems, etc., various animals and vegetables such as bacteria, algae and shell fish proliferated and slimes of these microorganisms were generated to cause various difficulties.

Accordingly, for controlling these microorganisms, various preservatives, antifungal agents, algicides, etc. for industrial use have been used as a slime control agent. However, it has been still desired to have a control agent which has effects against a broad spectrum of microorganisms at low concentration, and yet is high in safety.

SUMMARY OF THE INVENTION

An object of the present invention is to provide a dihydrobenzothazine and dihydrobenzooxazine derivative which is very effective as a microorganism control agent.

The compound of the present invention is a compound represented by the formula:

(I)

(wherein $R^1$ and $R^2$ each represent a hydrogen atom, a halogen atom, a nitro group, a lower alkyl group or a trifluoromethyl group; $R^3$ represents a hydrogen atom, a lower alkyl group, a phenyl group or a lower alkoxycarbonyl group; $R^4$ and $R^5$ each represent a hydrogen atom or a lower alkyl group; $R^6$ represents a halogen atom; and X represents an oxygen atom or a sulfur atom).

DESCRIPTION OF THE PREFERRED EMBODIMENTS

In the above formula, as the lower alkyl group represented by $R^1$, $R^2$, $R^3$, $R^4$ and $R^5$, methyl, ethyl, propyl, isopropyl, butyl, isobutyl, t-butyl, etc. may be included, particularly preferably methyl. As the halogen atom represented by $R^1$, $R^2$ and $R^6$, chlorine, bromine, fluorine and iodine may be included, particularly preferably chlorine and bromine. As the lower alkoxycarbonyl group represented by $R^3$, methoxycarbonyl and ethoxycarbonyl may be included.

The compounds of the formula (I) of the present invention are exemplified in Table 1.

TABLE 1

| Compound No. | X | $R^1$ | $R^2$ | $R^3$ | $R^4$ | $R^5$ | $R^6$ | Physical property (mp) |
|---|---|---|---|---|---|---|---|---|
| 1 | O | H | H | H | H | H | Cl | 107–109 |
| 2 | O | 6-CH$_3$ | H | H | H | H | Cl | 98–101 |
| 3 | O | 6-C$_2$H$_5$ | H | H | H | H | Cl | 87 |
| 4 | O | 6-iC$_3$H$_7$ | H | H | H | H | Cl | 95.6 |
| 5 | O | 6-CF$_3$ | H | H | H | H | Cl | 86–88 |
| 6 | O | 6-Cl | H | H | H | H | Cl | 90–92 |
| 7 | O | 6-Br | H | H | H | H | Cl | 96.6 |
| 8 | O | 6-CH$_3$ | 7-Cl | H | H | H | Cl | 98.6 |
| 9 | O | 6-CH$_3$ | 7-Br | H | H | H | Cl | 116.5 |
| 10 | O | 6-Cl | 7-CH$_3$ | H | H | H | Cl | 119.2 |
| 11 | O | 6-Br | 7-CH$_3$ | H | H | H | Cl | 138.6 |
| 12 | O | 6-Cl | 7-Cl | H | H | H | Cl | 103.5 |
| 13 | O | 6-Cl | 7-Br | H | H | H | Cl | 99–100 |
| 14 | O | 6-Br | 7-Cl | H | H | H | Cl | 121.3 |
| 15 | O | 6-Br | 7-Br | H | H | H | Cl | 107.1 |
| 16 | O | 6-Cl | 8-Cl | H | H | H | Cl | 111–113 |
| 17 | O | 6-Cl | 8-Br | H | H | H | Cl | 110–112 |
| 18 | O | 6-CH$_3$ | 8-Br | H | H | H | Cl | 71–73 |
| 19 | O | 7-NO$_2$ | H | H | H | H | Cl | 97.8 |
| 20 | S | H | H | H | H | H | Cl | $n_D^{25}$ 1.6281 |
| 21 | S | 6-Cl | H | H | H | H | Cl | 81.9 |
| 22 | O | 6-CF$_3$ | H | H | H | H | Cl | 108–110 |
| 23 | O | H | H | H | H | H | Br | 97.8 |
| 24 | O | 6-C$_2$H$_5$ | H | H | H | H | Br | 52.8 |
| 25 | O | 6-iC$_3$H$_7$ | H | H | H | H | Br | 59.3 |
| 26 | O | 7-NO$_2$ | H | H | H | H | Br | 97.8 |
| 27 | O | 6-CH$_3$ | 7-Cl | H | H | H | Br | 70.7 |
| 28 | O | 6-CH$_3$ | 7-Br | H | H | H | Br | 87.9 |
| 29 | O | 6-Cl | 7-Cl | H | H | H | Br | 112.5 |
| 30 | O | 6-Cl | 7-Br | H | H | H | Br | 96.6 |
| 31 | O | 6-Br | 7-CH$_3$ | H | H | H | Br | 81.3 |
| 32 | O | 6-Br | 7-Cl | H | H | H | Br | 92.3 |
| 33 | S | 6-Cl | H | H | H | H | Br | 77 |
| 34 | S | 6-CF$_3$ | H | H | H | H | Br | 89.7 |
| 35 | O | H | H | CH$_3$ | H | H | Cl | 100–102 |
| 36 | O | H | H | C$_2$H$_5$ | H | H | Cl | 76.3 |
| 37 | O | H | H | ph | H | H | Cl | 131–134 |
| 38 | O | 6-CH$_3$ | H | C$_2$H$_5$ | H | H | Cl | 66.4 |

TABLE 1-continued

| Compound No. | X | $R^1$ | $R^2$ | $R^3$ | $R^4$ | $R^5$ | $R^6$ | Physical property (mp) |
|---|---|---|---|---|---|---|---|---|
| 39 | O | 6-Cl | H | $C_3H_7$ | H | H | Cl | 76.3 |
| 40 | O | 6-Cl | H | $COOCH_3$ | H | H | Cl | 99–101 |
| 41 | O | H | H | $C_2H_5$ | H | H | Cl | $n_D^{27}$ 1.6026 |
| 42 | O | H | H | H | $CH_3$ | H | Cl | bp:133–135/2 mm Hg |
| 43 | O | H | H | H | $tC_4H_9$ | H | Br | 98.9 |
| 44 | O | H | H | H | $CH_3$ | $CH_3$ | Br | 96.2 |
| 45 | O | 6-Cl | H | H | $CH_3$ | $CH_3$ | Br | 136.2 |

A preferred group of compounds of the present invention are compounds wherein $R^1$ is hydrogen atom, methyl, ethyl, isopropyl, chlorine, bromine or trifluoromethyl and substituted at the 6-position, $R^2$ is hydrogen atom, chlorine, bromine or methyl and substituted at the 7-position, $R^3$ is hydrogen atom, methyl, ethyl, propyl, phenyl or methoxycarbonyl, $R^4$ and $R^5$ are hydrogen atoms, $R^6$ is chlorine or bromine, and X is oxygen atom or sulfur atom.

The compounds (I) of the present invention can be prepared according to the method shown by the following reaction schemes.

Method A:

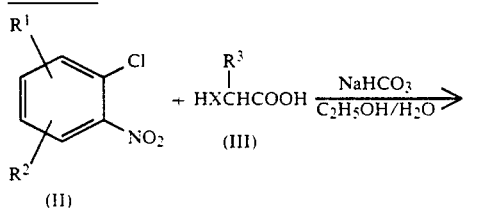
(II)      (III)

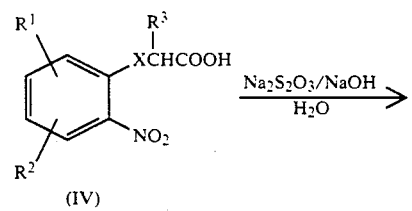
(IV)

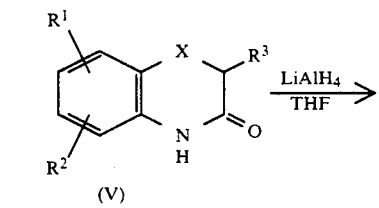
(V)

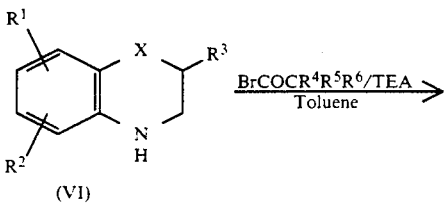
(VI)

Method A:
-continued

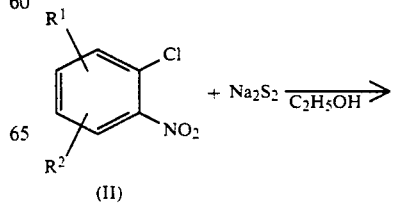
(VII)

The first step of reacting the compound (II) with the compound (III) to obtain the compound (IV) is a dehydrochlorination reaction, which is carried out by heating in a solvent in the presence of a base. The base to be used is not particularly limited, which is used as the deacidifying agent in conventional reactions, but may be preferably an alkali metal carbonate, an alkali metal hydrogen carbonate, an alkali metal hydride or an organic base such as triethylamine. The solvent to be used is not particularly limited, provided that it does not interfere with the reaction and can dissolve the starting materials to some extent, but may preferably include solvent mixtures of alcohols such as methanol, ethanol, isopropanol with water.

The second step of ring closing the compound (IV) to obtain the compound (V) is carried out under heating by adding sodium hydrosulfite little by little in water in the presence of a base.

The third step of eliminating the oxo group by reduction of the compound (V) to obtain the compound (VI) uses aluminum lithium hydride, and the solvent is not particularly limited, provided that it does not interfere with the present reaction, but may be preferably ethers such as tetrahydrofuran or dioxane.

The fourth step of acylating the compound (VII) to obtain the compound (VIII) is carried out in a solvent of an aromatic hydrocarbon such as benzene, toluene or xylene in the presence of an organic base such as pyridine or triethylamine.

Method B:

$$\underset{(II)}{\text{[structure]}} + Na_2S_2 \xrightarrow{C_2H_5OH}$$

Method B:

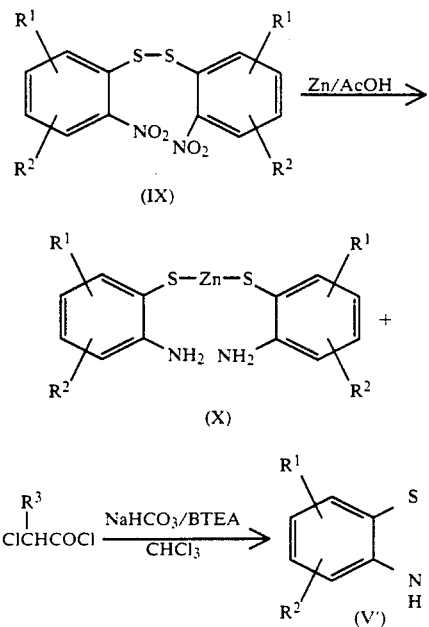

The reaction in the first step of thiolating the compound (II) to obtain the compound (IX) is carried out by heating under reflux while adding sodium disulfide little by little into the alcoholic solution of the compound (II).

The second step of reducing the compound (IX) into the compound (X) is carried out by adding zinc little by little into the compound (IX) suspended in acetic acid under heating to obtain the compound (X) as a zinc salt.

The reaction in the third step to ring close the compound (X) with acylation to obtain the compound (V') is carried out by dissolving the compound (X) and BTEA (benzyltriethylammonium chloride) in a halogenated hydrocarbon solvent such as trichloromethane and adding dropwise under heating chloroacetic chloride in the presence of a base such as sodium hydrogen carbonate.

The compound (V') can be derived to the desired compound (VI) similarly as in the third step in the method A.

The microorganism control agent of the present invention contains the compound of the formula (I) as the active ingredient. An amount of the compound of the formula (I) is preferably 0.1 to 95% by weight, more preferably 0.5 to 90% by weight based on the microorganism control agent. The compound (I) may be also used as itself, but generally used after preparation according to conventional methods into, for example, a powder, wettable agent, emulsion, fine particle, granule, etc., by formulating a carrier, surfactant, dispersant or auxiliary, etc. If necessary, it can be also formed into a slow-releasing preparation to maintain its activity for a long time.

The microorganism control agent of the present invention can be used as a control agent of slime and sludge generated in cooling water systems or paper making steps or as a preservative of resin emulsions, and exhibits a high control effect against a broad spectrum of microorganisms such as bacteria, mycelia, algae, etc. Particularly, it has excellent effects against algae such as blue algae, green algae, diatom, etc.; bacteria such as *Zoogrea, Spherotilus,* as well as molds such as water mold, blue mold, etc.

The use methods can include methods of supplying the chemicals to water systems according to various embodiments similarly as the slime control agent of the prior art. For example, there can be used the method in which the present agent is placed in a bag made of a water-permeable cloth or nonwoven fabric, or a molded product such as a tablet or granule is provided in water systems, or the method in which it is mixed into a coating material, etc.

The present invention is described below by referring to Examples.

EXAMPLE 1

The reaction between 115.2 g of 2,5-dichloronitrobenzene and 45.6 ml of thioglycolic acid was carried out by heating in 50% aqueous ethanol under alkaline conditions, and filtered when hot. The filtrate was returned to acidic, to yield precipitated crystals of 98 g of 4-chloro-2-nitriphenylthioacetate.

Subsequently, the above compound obtained was cyclized by the reaction under heating under alkaline conditions in the presence of sodium hydrosulfite, the reaction mixture was filtered when hot, and the filtrate was returned to acidic to give precipitated crystals of 21 g of 6-chloro-2H-1,4-benzothiazine-3-one.

Subsequently, the crystals were reduced with aluminum lithium hydride in tetrahydrofuran solvent, and further imino groups were bromoacetylated with the use of bromoacetyl bromide in the presence of pyridine. The product was extracted with toluene solvent, washed, purified, dried and the column was treated (Wako gel C-200) to obtain 5.95 g of the desired compound.

By NMR and MASS analyses, it was confirmed to be N-bromoacetyl-6-chloro-3,4-dihydro-2H-1,4-benzothiazine (Compound No. 33).

EXAMPLE 2

To a solution of 80 g of 2,5-dichloronitrobenzene dissolved in 300 ml of ethanol was added little by little equal amount of sodium disulfide, and the mixture was heated under reflux for 2 hours. The reaction mixture was cooled to room temperature and the crystals of bis(2-nitro-4-chlorophenyl)disulfide were separated by filtration. Yield 64.1%.

Next, 11.4 g of the crystals were suspended in 1,050 ml of acetic acid, and 60 g of zinc metal powder was added little by little under heating. After heating for 1 hour, 2 liters of hot water were added and the mixture was filtered when hot. The filtrate was cooled to give a zinc salt of 2-amino-4-chlorothiophenol at a yield of 80 %.

Next, 1.9 g of the above zinc salt and 2.28 g of BTEA were dissolved in 25 ml of trichloromethane, and 1.68 g of sodium hydrogen carbonate was added, followed by ice-cooling. To the mixture was added dropwise 5 ml of a solution of 1.36 g of chloroacetic chloride in trichloromethane over 20 minutes, and the mixture was stirred for one hour. Further, after stirring under heating at 55° C. for 8 hours, the solvent was removed, 40 ml of 1 N hydrochloric acid was added, and the crystals precipitated were separated by filtration. The crystals were recrystallized from ethanol to give 6-chloro-2H-1,4-benzothiazin-3-one at a yield of 80%.

Subsequently, the crystals were reduced in the same manner as in the final step of Example 1, and further bromoacetylated to give N-bromoacetyl-6-chloro-3,4-dihydro-2H-1,4-benzothiazine (Compound No. 33).

EXAMPLE 3

The reaction between 28.1 g of 2,5-dibromonitrobenzene and 7.6 g of glycolic acid was carried out by heating in a 70% aqueous ethanol solution under alkaline conditions to give 19.3 g of 4-bromo-2-nitrophenoxyacetic acid as precipitated crystals.

Subsequently, the above compound obtained was cyclized by the reaction under heating under alkaline conditions in the presence of sodium hydrosulfite, the mixture was filtered when hot and the filtrate was returned to acidic to give 10.8 g of 6-bromo-2H-1,4-benzoxazin-3-one as precipitated crystals.

Subsequently, the crystals were reduced with aluminum lithium hydride in tetrahydrofuran solvent, and further imino groups were chloroacetylated with the use of pyridine. The product was extracted with toluene, washed, dried, concentrated and then recrystallized from ethanol to give 10.4 g of N-chloroacetyl-6-bromo-3,4-dihydro-2H-benzoxazine (Compound No. 7).

EXAMPLE 4

Algicidal test

Test chemical

An emulsion comprising a wettable agent comprising 10.0% by weight of N-bromoacetyl-6-chloro-3,4-dihydro-2H-1,4-benzothiazine, 77.5% by weight of kaolin, 20.0% by weight of white carbon, 2.0% by weight of Neopelex (trade mark, Kao-Atlas, surfactant) and 0.5% by weight of Dumol EP (trade mark, Kao-Atlas, surfactant), and 10% by weight of the above active ingredient and 10% by weight of an emulsifier dissolved in xylene was employed.

Test method

In a sterilized laboratory dish made of stainless steel of 90 mm in diameter and 15 mm in depth, 10 ml of the agar medium shown below containing a predetermined concentration of the chemical solution was placed and solidified. A test algae cultured separately was coated on the agar medium, placed under a temperature of 25° C. and a light of 2,000 lux, and the growth of algae was observed 10 days after the treatment.

| Test algae: *Chlorella vulgaris* (green algae) | |
| --- | --- |
| Medium composition: | |
| $Ca(NO_3)_2.4H_2O$ | 15 mg |
| $KNO_3$ | 10 mg |
| $MgSO_4.7H_2O$ | 4 mg |
| Vitamin B12 | 0.01 μg |
| Biotin | 0.01 μg |
| Thiamine.HCl | 1 μg |
| PIV metal | 0.3 ml |
| $FeCl_3.6H_2O$ | 19.6 mg |
| $MnCl_2.4H_2O$ | 3.6 mg |
| $ZnSO_4.7H_2O$ | 2.2 mg |
| $CoCl_2.6H_2O$ | 0.4 mg |
| $Na_2EDTA.2H_2O$ | 100 mg |
| $Na_2MoO_4.2H_2O$ | 0.25 mg |
| Pure water | 100 ml |
| Tris(hydroxymthyl)aminomethane | 50 mg |
| Agar | 1.5 g |
| Pure water | 99.7 ml |
| pH 7.5 | |

| Test algae: *Phormidium foveolarum* (blue algae) | |
| --- | --- |
| Medium composition: | |
| $KNO_3$ | 100 mg |
| $MgSO_4.7H_2O$ | 25 mg |
| $K_2HPO_4$ | 25 mg |
| NaCl | 10 mg |
| $CaCl_2.2H_2O$ | 1 mg |
| Fe solution | 0.1 ml |
| $FeSO_4.7H_2O$ | 1 g |
| Pure water | 500 ml |
| Conc. $H_2SO_4$ | 2 drops |
| A5 solution | 0.1 ml |
| $H_3BO_4$ | 286 mg |
| $MnSO_4.7H_2O$ | 250 mg |
| $ZnSO_4.7H_2O$ | 22.2 mg |
| $CuSO_4.5H_2O$ | 7.9 mg |
| $Na_2MoO_4.2H_2O$ | 2.1 mg |
| Pure water | 100 ml |
| Agar | 1.5 g |
| Pure water | 99.8 ml |
| pH 8.0 | |

[Test results]

| Concentration (ppm) | *Chlorella vulgaris* | | *Phormidium foveolarum* | |
| --- | --- | --- | --- | --- |
| | Wettable agent | Emulsion | Wettable Agent | Emulsion |
| 0 | +++ | +++ | +++ | +++ |
| 0.08 | +++ | +++ | +++ | +++ |
| 0.16 | + | ++ | ++ | +++ |
| 0.31 | − | − | + | ++ |
| 0.63 | − | − | − | − |
| 1.25 | − | − | − | − |

Note: +++ Abundant growth, ++ Poor growth, + Very poor growth, − No growth

EXAMPLE 5

Antibacterial power against *Sphaerotilus natus*

Test method

In a sterilized laboratory dish made of stainless steel of 90 mm in diameter and 15 mm in depth, 10 ml of the agar medium shown below containing a predetermined concentration of the chemical compound (N-bromoacetyl-6-chloro-3,4-dihydro-2H-1,4-benzothiazine, Compound No. 33) was placed and solidified. Separately cultured *sphaerotilus natus* IFO-13543 microorganism was inoculated onto the agar medium, cultured under room temperature for 48 hours, and the growth of the microorganism was observed.

| Medium composition: | |
| --- | --- |
| Yeast extract | 2 g |
| Tripton (Difco) | 1 g |
| Sodium acetate | 1 g |
| Soil extract | 50 ml |
| Pure water | 950 ml |
| Agar | 20 g |
| pH | 7.4 |

| [Test results] | |
| --- | --- |
| Compound concentration (ppm) | Growth of Sphaerotilus |
| 0 | +++ |
| 5 | ++ |
| 10 | + |
| 50 | − |
| 100 | − |
| 500 | − |

+++ Abundant growth, ++ Poor growth, + Very poor growth, − No growth

We claim:

1. A compound represented by the formula:

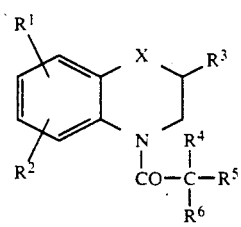

(I)

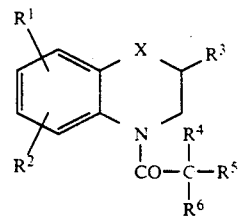

(I)

wherein $R^1$ and $R^2$ each represent a hydrogen atom, a halogen atom, a nitro group, a lower alkyl group or a trifluoromethyl group; $R^3$ represents a hydrogen atom, a lower alkyl group, a phenyl group or a lower alkoxycarbonyl group; $R^4$ and $R^5$ each represent a hydrogen atom or a lower alkyl group; $R^6$ represents a halogen atom; and X represents a sulfur atom, provided that $R^1$ and $R^2$, are not both hydrogen.

2. The compound according to claim 1, wherein $R^1$ is a hydrogen atom, a methyl group, an ethyl group, an isopropyl group, a chlorine atom, a bromine atom or a trifluoromethyl group and substituted at the 6-position.

3. The compound according to claim 1, wherein $R^2$ is a hydrogen atom, a chlorine atom, a bromine atom or a methyl group and substituted at the 7-position.

4. The compound according to claim 1, wherein $R^3$ is a hydrogen atom, a methyl group, an ethyl group, a propyl group, a phenyl group or a methoxycarbonyl group.

5. The compound according to claim 1, wherein $R^4$ and $R^5$ are both hydrogen atoms.

6. The compound according to claim 1, wherein $R^6$ is a chlorine atom or a bromine atom.

7. The compound according to claim 1, wherein $R^1$ is a hydrogen atom, a methyl group, an ethyl group, an isopropyl group, a chlorine atom, a bromine atom or a trifluoromethyl group and substituted at the 6-position; $R^2$ is a hydrogen atom a chlorine atom, a bromine atom or a methyl group and substituted at the 7-position; $R^3$ is a hydrogen atom, a methyl group, an ethyl group, a propyl group, a phenyl group or a methoxycarbonyl group; $R^4$ and $R^5$ are both hydrogen atoms; and $R^6$ is a chlorine atom or a bromine atom.

8. The compound according to claim 1, wherein the compound is N-bromoacetyl-6-chloro-3,4-dihydro-2H-1,4-benzothiazine.

9. The compound according to claim 1, wherein $R^2$ is selected from the group consisting of a halogen atom, a nitro group, a lower alkyl group and a trifluoromethyl group.

10. The compound according to claim 1, wherein $R^2$ is selected from the group consisting of a chlorine atom, a bromine atom and a methyl group and is substituted at the 7-position.

11. The compound according to claim 1, wherein $R^2$ is a chlorine atom and is substituted at the 7-position.

12. A microorganism control composition comprising an effective amount of a compound represented by the formula:

wherein $R^1$ and $R^2$ each represent a hydrogen atom, a halogen atom, a nitro group, a lower alkyl group or a trifluoromethyl group; $R^3$ represents a hydrogen atom, a lower alkyl group, a phenyl group or a lower alkoxy-carbonyl group; $R^4$ and $R^5$ each represent a hydrogen atom or a lower alkyl group; $R^6$ represents a halogen atom; and X represents a sulfur atom, provided that $R^1$ and $R^2$ are not both all hydrogen.

13. The microorganism control composition according to claim 12, wherein $R^1$ is a hydrogen atom, a methyl group, an ethyl group, an isopropyl group, a chlorine atom, a bromine atom or a trifluoromethyl group and substituted at the 6-position.

14. The microorganism control composition according to claim 12, wherein $R^2$ is a hydrogen atom, a chlorine atom, a bromine atom or a methyl group and substituted at the 7-position.

15. The microorganism control composition according to claim 12, wherein $R^3$ is a hydrogen atom, a methyl group, an ethyl group, a propyl group, a phenyl group or a methoxycarbonyl group.

16. The microorganism control composition according to claim 12, wherein $R^4$ and $R^5$ are both hydrogen atoms.

17. The microorganism control composition according to claim 12, wherein $R^6$ is a chlorine atom or a bromine atom.

18. The microorganism control composition according to claim 12, wherein $R^1$ is a hydrogen atom, a methyl group, an ethyl group, an isopropyl group, a chlorine atom, a bromine atom or a trifluoromethyl group and substituted at the 6-position; $R^2$ is a hydrogen atom, a chlorine atom, a bromine atom or a methyl group and substituted at the 7-position; $R^3$ is a hydrogen atom, a methyl group, an ethyl group, a propyl group, a phenyl group or a methoxycarbonyl group; $R^4$ and $R^5$ are both hydrogen atoms; and $R^6$ is a chlorine atom or a bromine atom.

19. The microorganism control composition according to claim 12, wherein the compound is N-bromoacetyl-6-chloro-3,4-dihydro-2H-1,4-benzothiazine.

20. The microorganism control composition according to claim 12, wherein the compound of formula (I) is in an amount of 0.1 to 95% by weight.

21. The microorganism control composition according to claim 12, wherein the compound of formula (I) is in an amount of 0.5 to 90% by weight.

22. A method of combatting microorganisms comprising applying to said microorganisms or to a locus thereof, an effective amount of a compound according to claim 1 alone or in admixture with a carrier.

23. The method according to claim 22, wherein the compound is N-bromoacetyl-6-chloro-3,4-dihydro-2H-1,4-benzothiazine.

* * * * *